(12) United States Patent
Mo et al.

(10) Patent No.: US 7,878,977 B2
(45) Date of Patent: Feb. 1, 2011

(54) FLEXIBLE ULTRASOUND TRANSDUCER ARRAY

(75) Inventors: Jian-Hua Mo, Milpitas, CA (US); Xuan-Ming Lu, San Jose, CA (US)

(73) Assignee: Siemens Medical Solutions USA, Inc., Malvern, PA (US)

( * ) Notice: Subject to any disclaimer, the term of this patent is extended or adjusted under 35 U.S.C. 154(b) by 978 days.

(21) Appl. No.: 11/242,175

(22) Filed: Sep. 30, 2005

(65) Prior Publication Data
US 2007/0078345 A1 Apr. 5, 2007

(51) Int. Cl.
*A61B 8/14* (2006.01)
(52) U.S. Cl. .................. 600/459; 600/466; 600/467
(58) Field of Classification Search .......... 600/437, 600/446, 473, 459, 466, 467
See application file for complete search history.

(56) References Cited

U.S. PATENT DOCUMENTS

| | | | |
|---|---|---|---|
| 5,471,988 A * | 12/1995 | Fujio et al. ............. | 600/439 |
| 5,526,814 A | 6/1996 | Cline et al. | |
| 5,655,535 A | 8/1997 | Friemel et al. | |
| 5,680,863 A | 10/1997 | Hossack et al. | |
| 5,967,989 A | 10/1999 | Cimochowski et al. | |
| 6,004,272 A | 12/1999 | Barry et al. | |
| 6,059,731 A * | 5/2000 | Seward et al. ......... | 600/459 |
| 6,120,453 A | 9/2000 | Sharp | |
| 6,292,433 B1 * | 9/2001 | Gilbert et al. ......... | 367/138 |
| 6,296,619 B1 * | 10/2001 | Brisken et al. ......... | 604/22 |
| 6,554,771 B1 | 4/2003 | Buil et al. | |
| 6,730,033 B2 | 5/2004 | Yao et al. | |
| 6,749,570 B2 | 6/2004 | Üstüner et al. | |
| 6,773,402 B2 * | 8/2004 | Govari et al. ......... | 600/459 |
| 6,788,967 B2 | 9/2004 | Ben-Haim et al. | |
| 6,824,516 B2 | 11/2004 | Batten et al. | |
| 2004/0002656 A1 | 1/2004 | Sheljaskow et al. | |
| 2004/0133105 A1 * | 7/2004 | Ostrovsky et al. ...... | 600/437 |
| 2004/0236223 A1 * | 11/2004 | Barnes et al. ......... | 600/459 |
| 2005/0148877 A1 * | 7/2005 | Guo et al. ............. | 600/459 |
| 2005/0215895 A1 * | 9/2005 | Popp et al. ............ | 600/437 |

FOREIGN PATENT DOCUMENTS

WO WO 99/48621 * 9/1999

OTHER PUBLICATIONS

"Adaptive Ultrasound Imaging System Using Large, Two-Dimensional, Conformal Arrays," by Pai-Chi Li, et al; 1994 Ultrasound Symposium; pp. 1625-1628.

"Phase Aberration Correction on Two-Dimensional Conformal Arrays," by Pai-Chi Li and Matthew O'Donnell; IEEE Transactions on Ultrasonics, Ferroelectrics, and Frequency Control, vol. 42, No. 1, Jan. 1995; pp. 73-82.

"A Flexible Ultrasonic Array Incorporating a Platelet Composite Transmitter—Theory and Experiment," by D. J. Powell and G. Hayward; 1993 Ultrasonics Symposium; pp. 687-690.

(Continued)

*Primary Examiner*—Eric F Winakur
*Assistant Examiner*—Katherine L Fernandez

(57) ABSTRACT

A transducer array includes two or more sub-arrays that move relative to each other. Position sensors on each of the sub-arrays provide spatial coordination for beamforming and/or image forming to yield extended field of view and high image resolution. The adaptable transducer array, such as mounted on a flexible transducer housing, allows the array to better conform to the patient during internal or external use.

29 Claims, 2 Drawing Sheets

OTHER PUBLICATIONS

"A Novel Ultrasound Array Incorporating Composite Transducer Technology," by D. J. Powell and G. Hayward; 1992 Ultrasonics Symposium; pp. 527-530.

"A Performance Appraisal of Flexible Array Structures Using a Facet Ensemble Scatting Technique," by D. J. Powell and G. Hayward, Ultrasound Research Group; 1991 Ultrasonics Symposium; pp. 753-756.

"Flexible Ultrasonic Transducer Arrays for Nondestructive Evaluation Applications—Part I: The Theoretical Modeling Approach"; David J. Powell and Gordon Hayward; IEEE Transaction on Ultrsonics, Ferroelectrics, and Frequency Control, vol. 43, No. 3, May 1996; pp. 385-392.

"Flexible Ultrasonic Transducer Arrays for Nondestructive Evaluation Applications—Part II: Performance Assessment of Different Array Configurations," by David J. Powell and Gordon Hayward; IEEE Transaction on Ultrsonics, Ferroelectrics, and Frequency Control, vol. 43, No. 3, May 1996; pp. 392-402.

"Phase Aberration Correction in Two Dimensions Using A Deformable Array Transducer," by Loriann L. Ries and Stephen W. Smith; 1995 IEEE Ultrasonics Symposium; pp. 1439-1442.

Three-Dimensional Ultrasound Imaging Using Multiple Magnetic Tracking Systems and Miniature Magnetic Sensors,: by D. F. Leotta, et al; 1995 Ultrasonics Symposium; pp. 1415-1418.

U.S. Appl. No. 11/181,520, filed Jul. 13, 2005.

* cited by examiner

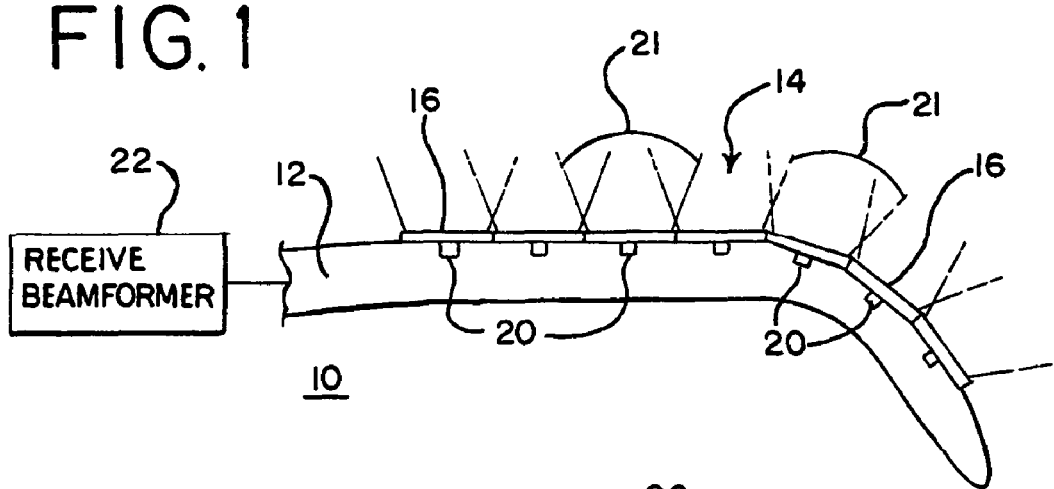
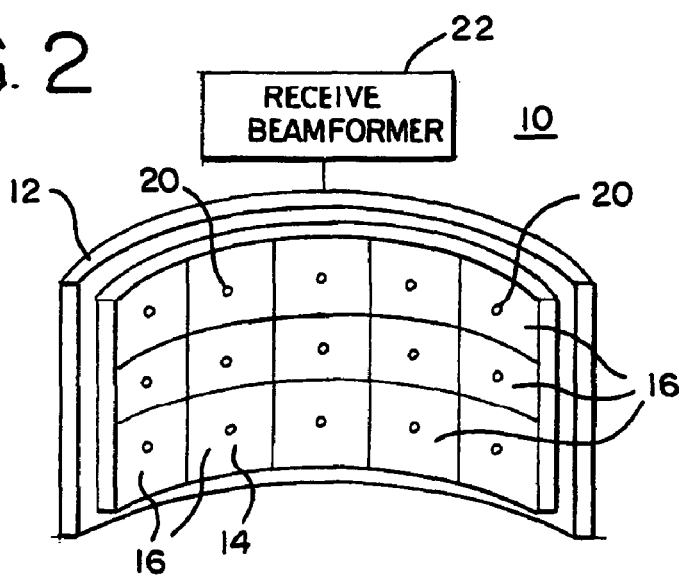
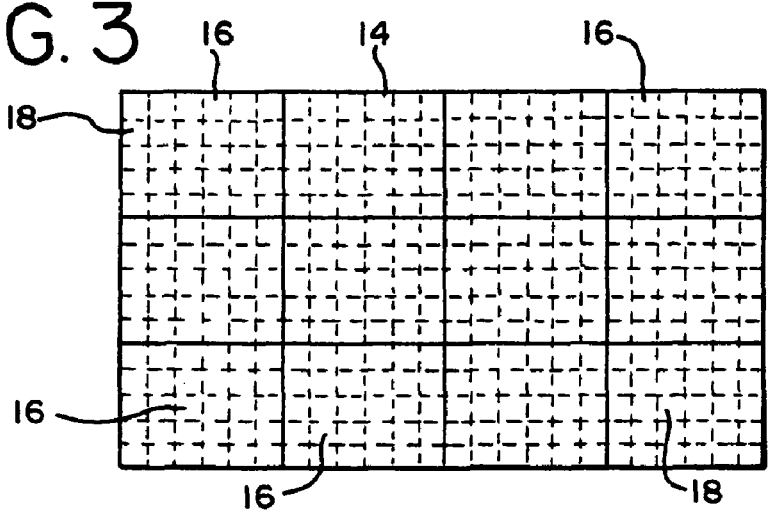

FLEXIBLE ULTRASOUND TRANSDUCER ARRAY

BACKGROUND

The present embodiments relate to medical ultrasound imaging. In particular, two or three dimensional ultrasound imaging has an extended field of view.

Many medical ultrasound arrays have a flat or convex acoustic window surface. This surface may not fit the body shape for scanning. Sonographers have to press and move the transducer probe to mate the probe to the surface of the patient. As a result, a scan and corresponding images may be difficult to reproduce. Such a probe may also cause sonographer discomfort. Multidimensional arrays, such as two dimensional arrays, may have even greater problems due to large surface area.

Some transducer arrays are on catheters or other probes for insertion into the patient. In order to accurately acquire and render imaging data, the distal "active imaging" portion of an ultrasound catheter probe or endoscope is usually straight and rigid. In applications where large field view and high resolution are desired, a large active imaging aperture is desired. Thus, the ultrasound catheter probe includes a long rigid portion at the distal end. This long rigid portion of a catheter probe creates difficulties for probe introduction and navigation, may cause patient discomfort, and may limit probe access to some clinical areas. When array length is not long enough to accommodate large field of view at the close-up range, the catheter is mechanically translated to form an extended view. However, the shape of the region of interest may change with the movement of catheter, making feature positions on the generated image inaccurate.

BRIEF SUMMARY

By way of introduction, the preferred embodiments described below include transducers, systems and methods for imaging with a flexible array. A transducer array includes two or more sub-arrays that move relative to each other. Position sensors on the sub-arrays provide spatial coordination for beamforming and/or image forming.

In a first aspect, an ultrasound transducer is provided for imaging. At least first and second sub-arrays each have a plurality of ultrasound transducer elements. The first and second sub-arrays are within or on a transducer housing and adjacent to each other. At least first and second position sensors are provided adjacent to the at least first and second sub-arrays, respectively. The transducer housing is operable to allow the first sub-array to change position relative to the second sub-array.

In a second aspect, an ultrasound transducer system is provided for imaging. A transducer housing has first and second transducer arrays of ultrasound transducer elements. The first transducer array is operable to move relative to the second transducer array. First and second position sensors are adjacent to the first and second transducer arrays. A receive beamformer connects with the first and second transducer arrays. The receive beamformer is operable to generate first samples from the first transducer array and generate second samples from the second transducer array.

In a third aspect, a method is provided for imaging with ultrasound. A transducer probe having first and second transducer arrays is positioned. The positioning allows movement of a first transducer array relative to a second transducer array. First acoustic echoes are received with the first transducer array. Second acoustic echoes are received with the second transducer array. A first position of the first transducer array is sensed. A second position of the second transducer array is sensed. An image is generated as a function of the first and second acoustic echoes and the first and second positions.

The present invention is defined by the following claims, and nothing in this section should be taken as a limitation on those claims. Further aspects and advantages of the invention are discussed below in conjunction with the preferred embodiments and may be later claimed independently or in combination.

BRIEF DESCRIPTION OF THE DRAWINGS

The components and the figures are not necessarily to scale, emphasis instead being placed upon illustrating the principles of the invention. Moreover, in the figures, like reference numerals designate corresponding parts throughout the different views.

FIG. 1 is a cross-sectional side view of one embodiment of a transducer probe with an adaptable array;

FIG. 2 is a perspective view of another embodiment of a transducer probe with an adaptable array;

FIG. 3 is a top view of one embodiment of a multidimensional array with sub-arrays of elements;

DETAILED DESCRIPTION OF THE DRAWINGS AND PRESENTLY PREFERRED EMBODIMENTS

Figure 4:
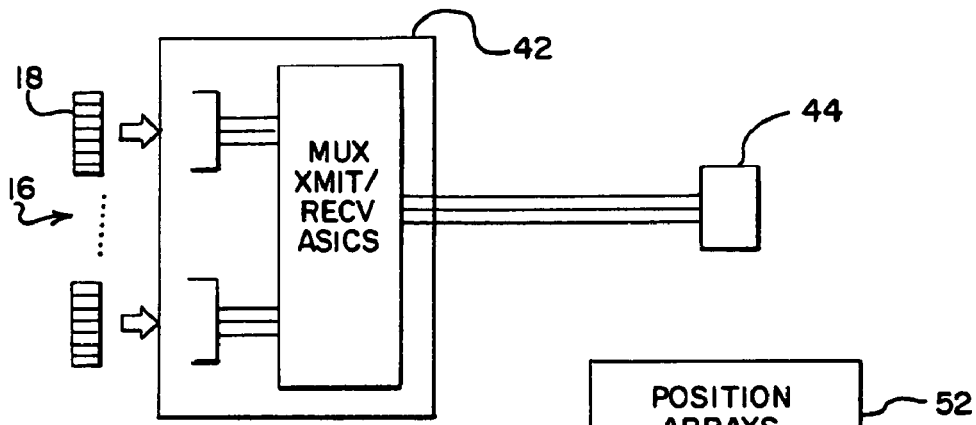
FIG. 4 is a block diagram of one embodiment of a sub-array module.

A flexible ultrasound catheter probe or endoscope has multiple segments, each of which contains an ultrasound transducer array and one or more position sensors. The flexible ultrasound catheter probe or endoscope generally conforms to the natural shape of a body cavity or surgical opening during introduction, navigation, and imaging. The position sensors provide position information of each segment and associated array, allowing multiple ultrasound transducer arrays to form a large imaging aperture or beamforming across arrays for maximum spatial bandwidth. Large-view 3D images may be constructed through rotation of this flexible ultrasound catheter probe or endoscope under the naturally conformed position.

An adaptable array may be used externally. For example, a multidimensional ultrasound transducer has I by J sub-arrays. Each sub-array is made of N by M elements. The surface of the array, such as joints or areas between sub-arrays, is bendable to fit a body contour. For example, bending occurs between the rigid sub-arrays. Each sub-array has a position sensor for beam forming and/or imaging reconstruction.

FIGS. 1 and 2 show ultrasound transducers and associated systems 10 for imaging. Other imaging modalities, such as optical, infrared or X-ray systems, may be used in alternative embodiments. The transducer systems 10 includes a transducer housing 12, a transducer array 14 with a plurality of sub-arrays 16 (multiple arrays 16) of elements 18, position sensors 20 and a receive beamformer 22. Additional, different or fewer components may be provided, such as providing a detector, scan converter and display in a medical diagnostic ultrasound imaging system.

The transducer housing 12 is metal, plastic, polymer, elastomer, fiberglass, fiber, nylon, combinations thereof or other now known or later developed materials. The material is flexible, stretchable and/or bendable to adapt to internal or external patient contours. Alternatively, the transducer housing 12 includes a hinge or joint for flexing or adapting to a contour. The transducer housing 12 is flexible at least between the transducer arrays or sub-arrays 16. The sub-arrays 16 change position relative to each other by flexing or bending of the transducer housing 12. By allowing the sub-arrays 16 to move relative to each other, the surface of the transducer array 14 is flexible or adapts to a contour.

FIG. 1 shows one embodiment of the transducer housing 12 being a probe operable for use within a patient. For example, the transducer housing 12 is a catheter, endoscope or intraoperative probe. The transducer housing 12 is polyurethane, pebax or other material with an appropriate softness to remain flexible for use as a catheter.

The transducer housing 12 includes at least a distal region for use within a patient. For example, an 8 French, 10 French or other sized catheter has a distal portion with multiple, such as seven, segments. Other numbers of segments or a catheter without defined segments may be used. Each of the segments is of a same or different length, such as each segment being about 7.5 mm long. Each segment includes one of the sub-arrays 16 and associated position sensors 20. For example, each segment contains an acoustic imaging array 16 of 7 mm in azimuthal by 2 or 2.5 mm in elevation, but other sizes may be used. The distal region, such as the portions joining segments between the sub-arrays 16 or the entire region, is flexible. The imaging portion of the catheter probe remains flexible for ease of introduction and navigation and for reducing patient discomfort.

The large imaging aperture provided by the array 14 increases spatial bandwidth as compared to a single rigid array, allowing large-view and high resolution images. For an ultrasonic transurethral catheter, a large imaging aperture, such as greater than 50 mm, may scan the whole prostate gland. Since the distal region with the array 14 is flexible, the catheter conforms, at least in part, to the natural bend of the urethral to reduce patient discomfort during imaging. In IVUS and/or intra-cardiac applications, the flexible catheter accesses hard-to-access areas to acquire images over a large vascular or cardiac region.

FIG. 2 shows an array 14 for external use. The transducer housing 12 is a flexible substrate, such as a sheet of Kapton polyimide film or a thin flexible PWB that is bendable and, optionally, provides electric connection. The sheet of material connects with the sub-arrays 16. Alternatively, a plurality of rigid sections connects together with flexible material or hinges. In one embodiment, a glue-like or sticky gel attaches the probe to the body surface or skin and couples sound waves to the body. The sonographer positions the transducer housing 12 and array 14 on a neck, arm, leg, torso, breast or other surface of a patient. The flexible material conforms to the contour of the patient by bending at least between the sub-arrays 16. Constant repositioning by hand may be avoided or reduced, more likely providing a consistent scan and corresponding image, and reducing sonographer scanning discomfort.

In another embodiment, the flexible portion of the transducer housing 12 shown in FIG. 2 is a surface or structure within a handheld probe. Air, gas, liquid, gel, springs or other devices or materials are within the transducer housing 12 to limit or allow flexing. The user applies pressure to the transducer housing 12 while holding the probe against a patient. In response to the pressure, the portion of the transducer housing 12 at the array 14 flexes to better conform to the contours of the user.

The array 14 includes a plurality of elements 18. The elements are piezoelectric, microelectromechanical (i.e. CMUT), piezo composite or other now known or later developed transducer material. The array 14 is a linear, curved linear, phased, one dimensional, two dimensional, multidimensional or other distributions of elements 18. For example, the array 14 is a linear array with 32 elements or a phased array with 64 elements on a catheter. In the embodiment of FIG. 3, the array 14 is a multidimensional array. The distribution and size of the elements 18 are for 7 MHz, a 10 MHz, a 14 MHz, or other imaging frequencies. Rectangular, hexagonal, triangular, sparse, fully sampled or other distributions of elements 18 and/or associated element shapes may be used.

The array 14 includes two or more sub-arrays 16. For example, FIG. 1 shows seven sub-arrays 16 forming a one-dimensional array 14. In other examples, FIGS. 2 and 3 show fifteen and twelve sub-arrays 16, respectively, in I by J arrangements (e.g., 5 by 3 or 4 by 3). Each of the sub-arrays 16 includes a plurality of elements 18, such as two or more elements 18. For example, two or more elements 18 are distributed in a linear or one dimensional sub-array 16. As another example, M by N elements 18 are provided in each sub-array 16. Each sub-array 16 may have a same or different number of elements 18 in a same or different distribution pattern.

The sub-arrays 16 are within or on the transducer housing 12. The sub-arrays 16 are rigid, but may be more or less flexible than the connected portion of the transducer housing 12. In one embodiment, the sub-arrays 16 are relatively rigid in comparison to the transducer housing 12 between the sub-arrays 16. In the catheter embodiment of FIG. 1, the overall catheter distal portion is flexible, but each array 16 is rigid. One array 16 moves relative to another transducer array 16 due to the bendable connection or flexing of the transducer housing 12.

The sub-arrays 16 are adjacent to each other. An edge of one sub-array 16 abuts or is next to an edge of another sub-array 16. For example, each sub-array 16 is within two element widths of another sub-array 16. Greater or lesser separation may be provided. For example, one or more of the sub-arrays 16 are spaced by more than two element widths from the closest sub-array 16. The spacing between different pairs of adjacent sub-arrays 16 is the same or different.

The sub-arrays 16 are fixedly mounted to or connected with the transducer housing 12. For example, the array 14 is mounted to a support structure underneath an outer covering of the transducer housing 12. The outer covering bonds to or rests against the array 14. As another example, the array 14 connects with a flexible acoustic window where the acoustic window connects to the remainder of the transducer housing 12.

In one embodiment, one or more of the sub-arrays 16 are replaceable within or on the transducer housing 12. Each sub-array 16 plugs in and out from the transducer housing 12. Snap fit, bolts, screws, dissolvable glue, or another connector releasably holds each sub-array 16 in position relative to the transducer housing 12. Electrical connections may be modular or include a mating structure. FIG. 4 shows one embodiment of a modular sub-array 16. The sub-array 16 connects with an application specific integrated circuit, processor or other circuit 42 for reducing channel count. Using time division multiplexing, partial beamforming or other channel reduction technique, the circuit 42 provides signals on a fewer number of conductors than elements 18 to the releasable electrical connector 44. A circuit 42 without channel reduction may be provided. Removable sub-arrays 16 allow for repair and ease of manufacturing. A same base transducer housing 12 is used for probes operating at different frequencies by changing the sub-arrays 16. The same transducer housing 12 may be used for different applications, including switching between 1D, 1.25D, 1.5D, 1.75D and 2D arrays 14.

The position sensors 20 are relative or absolute position sensors. Relative position sensors include strain gauges or other sensors for determining position relative to another object or location of the sensor. Absolute position sensors include magnetic position sensors or other sensors for determining a location in a common frame of reference or global coordinates. For example, miniature magnetic position sensors by Biosens or Ascension are used.

One or more position sensors 20 are adjacent to each sub-array 16. The position sensors 20 provide a location and/or orientation of each sub-array 16 for beam forming and/or image formation. A single or multiple position sensors 20 determine orientation and/or location. The position sensors 20 track or locate each sub-array 16, allowing a large imaging aperture and/or beamforming across multiple transducer arrays 16. The position information may determine locations for three-dimensional imaging.

The receive beamformer 22 includes a plurality of amplifiers, delays, phase rotators and one or more adders. Additional, different or fewer components may be provided, such as a multiplexer for time division multiplexing or switches for sub-array mixing. The same or different receive beamformer 22 connects with each of the sub-arrays 16. The receive beamformer 22 is located in an imaging system, in the transducer housing 12 or at both locations. For example, partial beamforming or sub-array mixing is performed in the transducer housing 12 with further beamforming being remote from the transducer housing 12. In the embodiment shown in FIG. 4, the circuit 42 includes multiplexers to switch among sub-arrays 16 to reduce the channel count for any cable and imaging system. Transmit and receive circuits for generating transmit waves and beamforming for a given sub-array module are also within the transducer housing 12.

Using signals from each channel or element 18, the receive beamformer 22 generates samples. The samples are generated from signals from different sub-arrays 16. For example, the receive beamformer 22 generates one set of samples from one transducer array 16 and generates another set of samples from another transducer array 16. FIG. 1 shows overlapping fields of view 21 for the different sub-arrays 16. Each sub-array 16 is used to beamform samples representing locations within the field of view 21 for the respective sub-array 16. The delay and sum or frequency based beamformation is handled separately for each sub-array 16. A processor uses the locations of the sub-arrays 16 to combine the fields of view 21 and associated data into an extended field of view. The combination is performed prior to or after detection.

As another example, one or more samples are responsive to an aperture that includes at least one element 18 from each of different sub-arrays 16. Channels from two or more sub-arrays 16 contribute to beamformation of the samples. The relative delays or phasing between channels is a function of the positions of the channels. Since elements 18 for different sub-arrays 16 may have different positions based on the relative position of the sub-arrays 16, the locations from the position sensors 20 of the sub-arrays 16 determine, in part, the relative delays or phasing.

The transmit beam can be formed with one or more sub-arrays 16. Some or all of the sub-arrays 16 may receive spontaneously. Alternatively, one or more sub-arrays 16 receive in sequence with system and cable channels switched among the sub-arrays 16.

Figure 5:
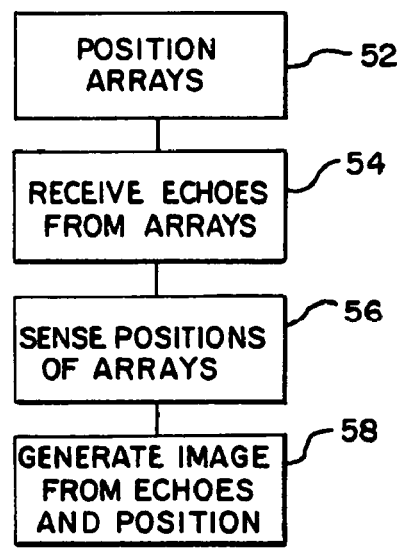
FIG. 5 is a flow chart diagram of one embodiment of a method for imaging with an adaptable transducer array.

FIG. 5 shows one embodiment of a method for imaging with ultrasound using an adaptive array. The transducers of FIGS. 1-4 or other transducers implement the method. Additional, different or fewer acts may be provided. The same or different order may be used, such as sensing positions in act 56 at a same time, after or prior to receiving echoes in act 54.

In act 52, a user positions a transducer probe. The transducer probe has a plurality of transducer arrays. The positioning allows movement of one transducer array relative to another transducer array. For example, the transducer probe is within a cavity, vessel or other portion internal to a patient. Due to the shape of the cavity, vessel or other portion, the transducer probe may flex for ease of positioning or patient comfort. The transducer probe may be steered to provide a desired position. Due to the shape or steering, the transducer probe and associated transducer arrays adapt. As another example, the transducer probe is attached adjacent to the skin of a patient, such as with a glue, bonding agent or gel. Since the skin of the patient may curve, the transducer probe conforms to the skin, resulting in relative movement or positioning of the transducer arrays by flexing of the transducer probe. As another example, the user places the transducer probe adjacent to the user. By applying pressure to the transducer probe, the transducer arrays move relative to each other to conform to the contour of the patient.

In act 54, acoustic echoes are received by the transducer arrays. The same or different transducer arrays or apertures are used for transmit as used in receive. The different arrays sequentially or simultaneously receive the acoustic echoes in response to transmissions. The transducer arrays sparsely or fully sample.

In act 56, sensors determine the position of the transducer arrays. The position is continuously or periodically determined. The determination may be at a same time, before or after the transducer array receives echoes. For example, the position is determined for each transmit or receive operation performed by a given transducer array. If the transducer arrays are used sequentially, the positions are determined sequentially. If the transducer arrays are used at a same time, the positions are sensed at the same time.

Figure 6:
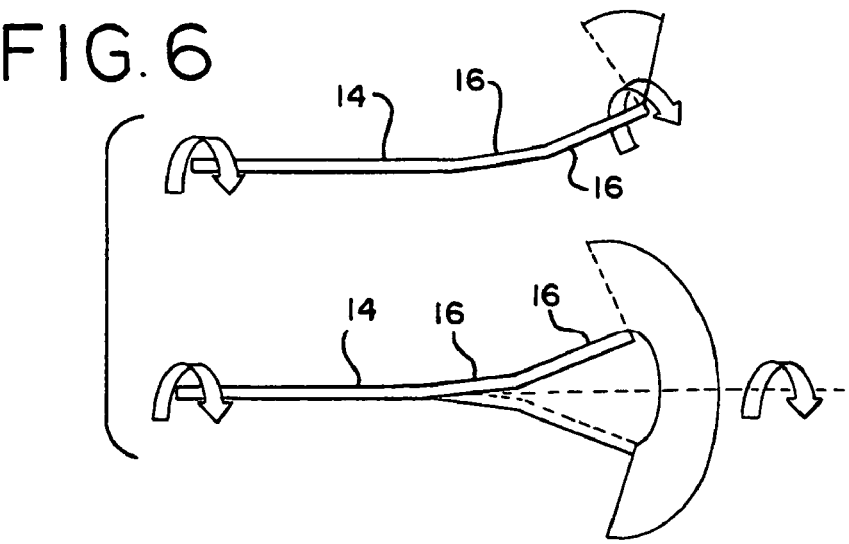
FIG. 6 is a representation of three dimensional scanning with the adaptable array of FIG. 1.

The sensors sense an absolute position, such as a position relative to a global or general coordinate system. Alternatively, the sensors sense a relative position. The position includes orientation, location or both orientation and location. For example, FIG. 6 shows the transducer array 14 with sub-arrays 16. The transducer array 14 is rotated to scan a volume for three dimensional imaging. The array 14 scans a plane at each rotational position or as the array 14 rotates. The data for the scan planes is assembled based on the position of the sub-arrays 16 during acquisition. A three dimensional representation is assembled from the data. Since multiple sub-arrays 16 are used, the scanned volume and associated three dimensional representation have an extended field of view.

In act 58 of FIG. 5, an image is generated as a function of the acoustic echoes received in act 54 and the positions sensed in act 56. The acoustic echoes for each transducer array are separately beamformed. The position information aligns the separate fields of view into an extended field of view. The position of the transducer arrays determines the positions of the fields of view. The beamformed data for the fields of view are combined. Alternatively, the position information indicates a relative position of different elements in an aperture including elements from two or more arrays. The relative position of the elements determines a distance to a transmit or receive focal region. The distance determines the relative delay and/or phasing used for beamformation. In another alternative embodiment, the position information is for beamformation and for combination of fields of view.

While the invention has been described above by reference to various embodiments, it should be understood that many changes and modifications can be made without departing from the scope of the invention. It is therefore intended that the foregoing detailed description be regarded as illustrative rather than limiting, and that it be understood that it is the following claims, including all equivalents, that are intended to define the spirit and scope of this invention.

We claim:

1. An ultrasound transducer for imaging, the transducer comprising:
   a transducer housing;
   at least first and second sub-arrays each having a plurality of ultrasound transducer elements on a fully sampled grid, the first and second sub-arrays within or on the transducer housing and adjacent to each other on first and second segments, respectively; and
   at least first and second position sensors adjacent to the at least first and second sub-arrays, respectively, wherein the transducer housing is configured to allow the first sub-array to change position relative to the second sub-array in response to the transducer housing conforming, at least in part, to fit a body contour of the patient, the change in position being by an amount that is a function of the body contour, the transducer housing conforming to fit the body contour during scanning with the ultrasound transducer elements for imaging, the amount different for different body contours, the change in position occurring between the first and second segments where the first and second sub-arrays are relatively rigid.

2. The transducer of claim 1 wherein the transducer housing comprises a catheter, endoscope, or intraoperative transducer housing, the at least first and second sub-arrays being adjacent in a distal region of the transducer housing, the distal region being operable for use within a patient.

3. The transducer of claim 2 wherein the first and second sub-arrays comprises one dimensional arrays.

4. The transducer of claim 2 wherein the transducer housing comprises the catheter and the distal region of the transducer housing is flexible at least between the first and second sub-arrays.

5. The transducer of claim 2 wherein the distal region comprises at least the first and second segments, the first sub-array and first position sensor in the first segment and the second sub-array and second position sensor in the second segment.

6. The transducer of claim 1 wherein the transducer housing comprises a flexible substrate connected with the first and second sub-arrays.

7. The transducer of claim 1 wherein the plurality of ultrasound transducer elements of the first and second sub-arrays each comprise a multidimensional array N×M elements where N and M are greater than one, the first sub-array having a same or different values of N or M.

8. The transducer of claim 1 wherein the first and second sub-arrays are relatively rigid in comparison to the transducer housing connection of the first sub-array to the second sub-array.

9. The transducer of claim 1 wherein the first sub-array is operable to be replaceable within or on the transducer housing.

10. The transducer of claim 1 wherein the first and second position sensors comprise magnetic position sensors.

11. The transducer of claim 1 further comprising:
    a receive beamformer connected with the first and second sub-arrays, the receive beamformer operable to generate samples from the first sub-array and generate samples from the second sub-array.

12. The transducer of claim 11 wherein the receive beamformer is at least in part within the transducer housing.

13. The transducer of claim 1 wherein the first sub-array being adjacent to the second sub-array comprises a first edge of the first sub-array being within two element widths of a second edge of the second sub-array.

14. The transducer of claim 1 wherein the first sub-array being adjacent to the second sub-array comprises a first edge of the first sub-array being more than two element widths away from a second edge of the second sub-array.

15. An ultrasound transducer system for imaging, the ultrasound transducer system comprising:
    a transducer housing having first and second transducer arrays of ultrasound transducer elements, the first transducer array operable to move passively, during imaging, relative to the second transducer array by an amount to adapt to a natural contour of a patient, the amount being different for different contours, the first and second transducer arrays being on rigid segments separated by a location of the passive movement of the first transducer array relative to the second transducer array;
    first and second position sensors adjacent to the first and second transducer arrays; and
    a receive beamformer connected with the first and second transducer arrays, the receive beamformer operable to generate first samples from the first transducer array and generate second samples from the second transducer array, the generation of the first samples, the sample locations of the first samples relative to the second samples, or both being a function of output from the first and second position sensors.

16. The ultrasound transducer system of claim 15 wherein the transducer housing comprises a probe operable for use within a patient, the first and second transducer arrays being adjacent in a distal region of the probe, the distal region being operable for use within a patient.

17. The ultrasound transducer system of claim 15 wherein the first and second transducer arrays comprise one or multi-dimensional arrays.

18. The ultrasound transducer system of claim 15 wherein the first transducer array is adjacent to the second transducer array, and wherein the transducer housing is flexible at least between the first and second transducer arrays.

19. The ultrasound transducer system of claim 15 wherein the transducer housing comprises a flexible substrate connected with the first and second transducer arrays in a handheld probe operable for use outside a patient.

20. The ultrasound transducer system of claim 15 wherein the first and second transducer arrays are operable to be replaceable within or on the transducer housing.

21. The ultrasound transducer system of claim 15 wherein the receive beamformer is at least in part within the transducer housing.

22. The ultrasound transducer system of claim 15 wherein the first samples are responsive to an aperture including at least one element from each of the first and second transducer arrays, at least one relative delay or phase of the receive beamformer being responsive to the first and second position sensors.

23. The ultrasound transducer system of claim 15 further comprising a processor operable to use the first and second samples for an image, a relative position of data in the image responsive to the first and second samples being a function of output from the first and second position sensors.

24. A method for imaging with ultrasound, the method comprising:

positioning a transducer probe having first and second transducer arrays at a location for imaging, wherein the positioning causes movement of a first transducer array relative to a second transducer array to conform, at least in part, to a contour of a patient at the location, the movement being due to change from another contour to the contour, the first and second transducer arrays being rigid in comparison to a location of the movement of the first transducer array relative to the second transducer array;

receiving first acoustic echoes with the first transducer array at the location;

receiving second acoustic echoes with the second transducer array;

sensing a first position of the first transducer array;

sensing a second position of the second transducer array; and generating an image as a function of the first and second acoustic echoes and the first and second positions.

25. The method of claim 24 wherein sensing the first and second positions comprises sensing absolute positions.

26. The method of claim 24 wherein positioning the transducer probe comprises positioning the transducer probe within a patient.

27. The method of claim 24 wherein positioning the transducer probe comprises attaching the transducer probe adjacent to skin of a patient.

28. The method of claim 24 wherein generating the image comprises generating the image from data beamformed separately from the first and second transducer arrays with corresponding positions of the data being a function of the first and second positions.

29. The method of claim 24 wherein generating the image comprises forming a beam with the first and second acoustic echoes with delays, phases or delays and phases being a function of the first and second positions.

* * * * *